US006213954B1

(12) United States Patent
Chen

(10) Patent No.: US 6,213,954 B1
(45) Date of Patent: Apr. 10, 2001

(54) PULSE METER

(76) Inventor: Tong-Pie Chen, 1F, 278 Chung Shan Rd., Sanchung, Taipei Hsien (TW)

( * ) Notice: Subject to any disclaimer, the term of this patent is extended or adjusted under 35 U.S.C. 154(b) by 0 days.

(21) Appl. No.: 09/249,775

(22) Filed: Feb. 16, 1999

(51) Int. Cl.[7] .................................................. A61B 5/00
(52) U.S. Cl. .......................... 600/500; 600/185; 377/15; 235/64
(58) Field of Search .................................. 600/485, 500; 377/15; 235/64

(56) References Cited

U.S. PATENT DOCUMENTS

| | | | | |
|---|---|---|---|---|
| 3,617,708 | * | 11/1971 | Bongiovanni | 377/215 |
| 3,843,047 | * | 10/1974 | Otsuka et al. | 235/64 |
| 4,993,050 | * | 2/1991 | Carpenteri et al. | 377/15 |
| 5,215,097 | * | 6/1993 | Watabe | 600/502 |

* cited by examiner

*Primary Examiner*—Robert L. Nasser
(74) *Attorney, Agent, or Firm*—Jacobson, Price, Holman & Stern, PLLC

(57) ABSTRACT

Accordingly, the object of the present invention is to provide a pulse meter comprising a pen body installed with a counting microprocessor, and a liquid crystal display (LCD) and a counter are installed on the proper position of the pen body. The counting microprocessor is connected with the LCD and the counting key. One hand may press a tested person or a patient for sensing the beat of the pulse thereof, and the other hand serves to press a counting key to count the times of the pulse, and thus the frequency of the pulse can be input into the counting microprocessor. Next, the counting microprocessor can derive the pulse number per minute and then display the result in the LCD. Since only a short period of pulse beat is necessary to be input the counting microprocessor. Thus the pulse frequency can be derived in a very short time and much time is saved. A switching key and time adjusting key are installed on the pen body, thus the counting microprocessor can be switched to a time display mode by the switching key. Thus, when the pulse meter is not used, it can be used as a clock for showing time.

1 Claim, 4 Drawing Sheets

PULSE METER

BACKGROUND OF THE INVENTION

1. Field of the Invention

The present invention relates to a pulse meter, especially to pulse meter having a pen body with a counting microprocessor, a liquid crystal display, and a counter. In using, one hand may press a tested person or a patient for sensing the beat of the pulse thereof, and the other hand serves to press a counting key to count the times of the pulse, and thus the frequency of the pulse can be input to the counting microprocessor, next, the counting microprocessor can derive the pulse number per minute and then display the result in the LCD.

2. Description of the Prior Art

In the hospital, when measuring the pulse of a patient, nurse usually holds the wrist of the patient, then see the clock through a minute, and at the same time, counts the times of the pulse. Therefore, she estimates the times of the pulse beat within a minute and records the data as a reference in medical diagnose.

However, since the nurse counts the pulse in mind, if at this time, she is called by a doctor or the patient's family or other nurse, the counting work is easily interrupted. Then, she is necessary to recount the pulse frequency.

Moreover, although a minute is not a long time, it is difficult to retain a steady count within one minute, especially to a busy nurse, this is a hard work. Therefore, it is probable that she forgets the count number during counting and then must recount the pulse number. This will waste much time. Moreover, it is possible that an error is generated during counting by carelessness.

Further, when a nurse tours the sickrooms, often she needs to measure the pulse of the patients. This is a busy work. If there are many patients. Then the overall measuring time is very long. She also needs to answer the questions of the patient's family and console the patients. Thus, a tour must waste a great deal of time. In measuring the pulse, if the work is performed successfully, one minute is necessary, however, if it cannot do well, for example, the aforementioned conditions are occurred, then much time are required. However, the work of a nurse is not only to measure the pulse of patients, but also many works are necessary to be processed. As a result, she must exactly control the working time.

Alternatively, although the medical equipment is improved continuously. The instruments for measuring pulses have been commercial sold in the markets. While these equipment is only suitable for the patients with serious disease since it is expensive. Most patients with sliglhtly disease unnecessarily use this equipment. The conventional pulse meter is sufficient. But as that aforesaid, to measuring pulses by human labor will need much time, and further many errors are easily occurred. Thus, it is necessary to be improved.

SUMMARY OF THE INVENTION

Accordingly, the object of the present invention is to provide a pulse meter comprising a pen body installed with a counting microprocessor, and a liquid crystal display (LCD) and a counter are installed on the proper position of the pen body. The counting microprocessor is connected with the LCD and the counting key. One hand may press a tested person or a patient for sensing the beat of the pulse thereof, and the other hand serves to press a counting key to count the times of the pulses, and thus the frequency of the pulses can be input into the counting microprocessor. Next, the counting microprocessor can derive the pulse number per minute and then display the result in the LCD. Since only a short period of pulse besting is necessary to be input the counting microprocessor. Thus the pulse frequency can be derived in a very short time and much time is saved. A switching key and time adjusting key are installed on the pen body, thus the counting microprocessor can be switched to a time display mode by the switching key. Thus, when the pulse meter is not used, it can be used as a clock for showing time.

The present invention will be better understood and its numerous objects and advantages will become apparent to those skilled in the art by referencing to the following drawings in which:

DETAILED DESCRIPTION OF THE PREFERRED EMBODIMENT

Figure 1:
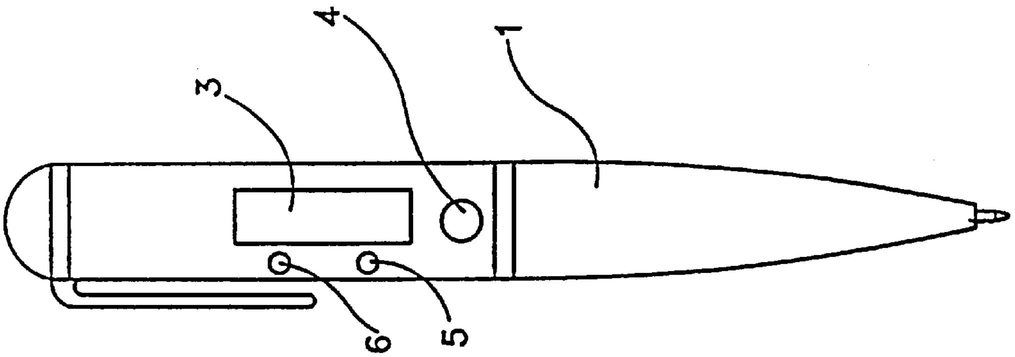
FIG. 1 is a front view of the present invention.
Figure 2:
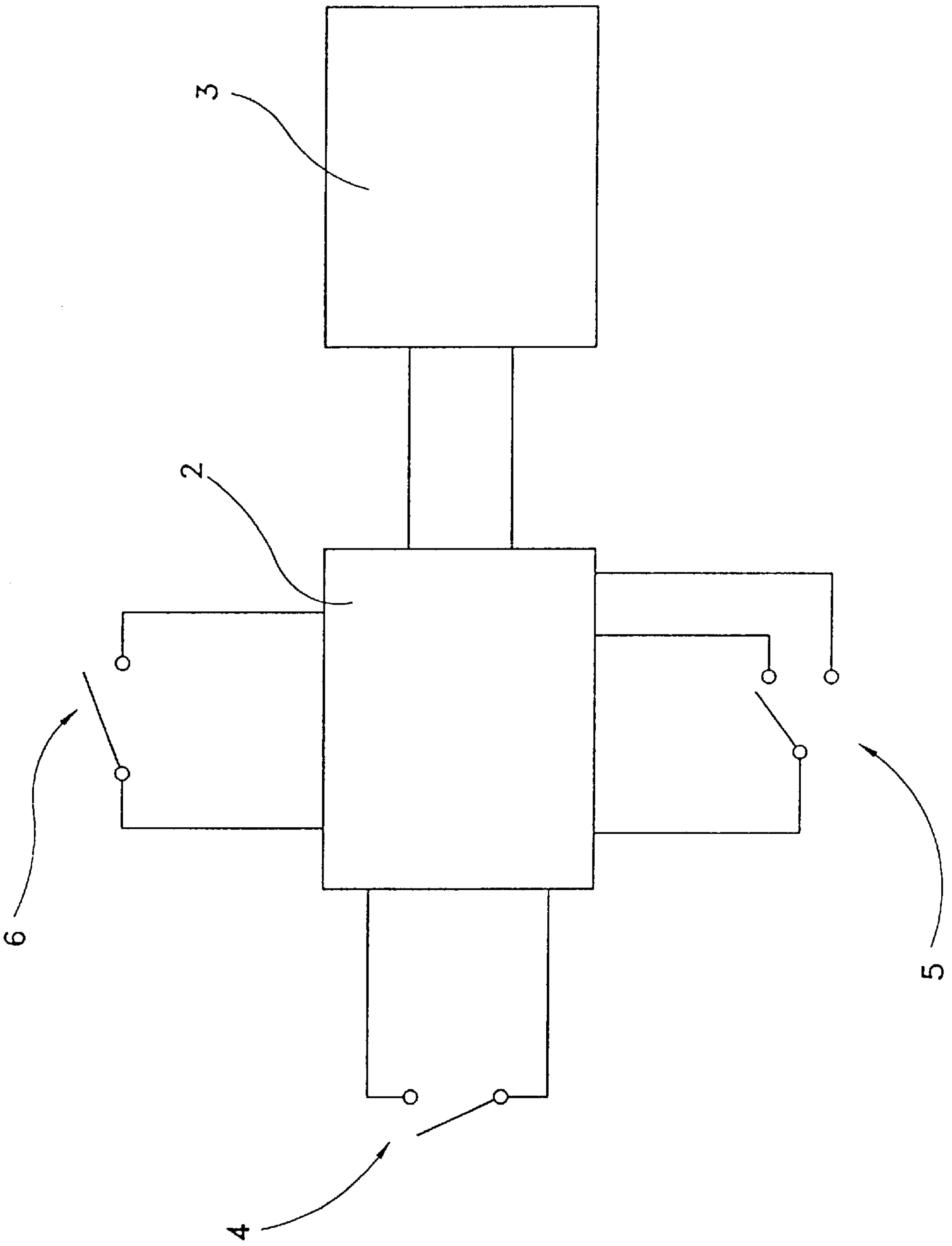
FIG. 2 is a circuit block diagram of the present invention.

As shown in FIG. 1 and 2, the present invention is illustrated. In the present invention, a counting microprocessor 2 is installed within a pen body 1. Further, a liquid crystal display 3 and a counting key 4 are installed in the proper position of the pen body. The counting microprocessor 2 is connected to the LCD 3 and the counting key 4.

According to the aforementioned structure, one hand may press a tested person or a patient for sensing the beat of the pulse thereof, and the other hand serves to press the counting key 4 to count the times of the pulse. The frequency of the pulse can thus be input to the counting microprocessor 2. Next, the counting microprocessor 2 can derive the pulse number per minute and then display the result in the LCD 3.

Since only a short period of pulse beat is necessary to be input to the counting microprocessor 2 for deriving the pulse number per minute. Thus the pulse frequency can be derived in a very short time and much time is saved.

Since when counting the pulse, by pressing the counting key 4, the pen body 1 causes the counting microprocessor 2 to count. The counting by memory of people is unnecessary. Therefore, errors can be avoided.

Moreover, although the beating of pulse is not absolute, only a small period of pulse is necessary to input the counting microprocessor and then it is converted as the pulse per minute which is very near the real pulse. Therefore, it is very accurate from the viewpoint of statistics and it is more accurate then counting by human.

With reference to FIG. 2, a switching key 5 is installed on the pen body 1 and a time adjusting key 6 connected to the counting microprocessor 2. Further, the counting microprocessor 2 has a clock. Through a switching key, the pulse counting mode can be changed as a time display mode and then the time is displayed on the LCD 3. Thus, the present invention not only can be used to count the pulse frequency, but also used to Display time.

Figure 3:
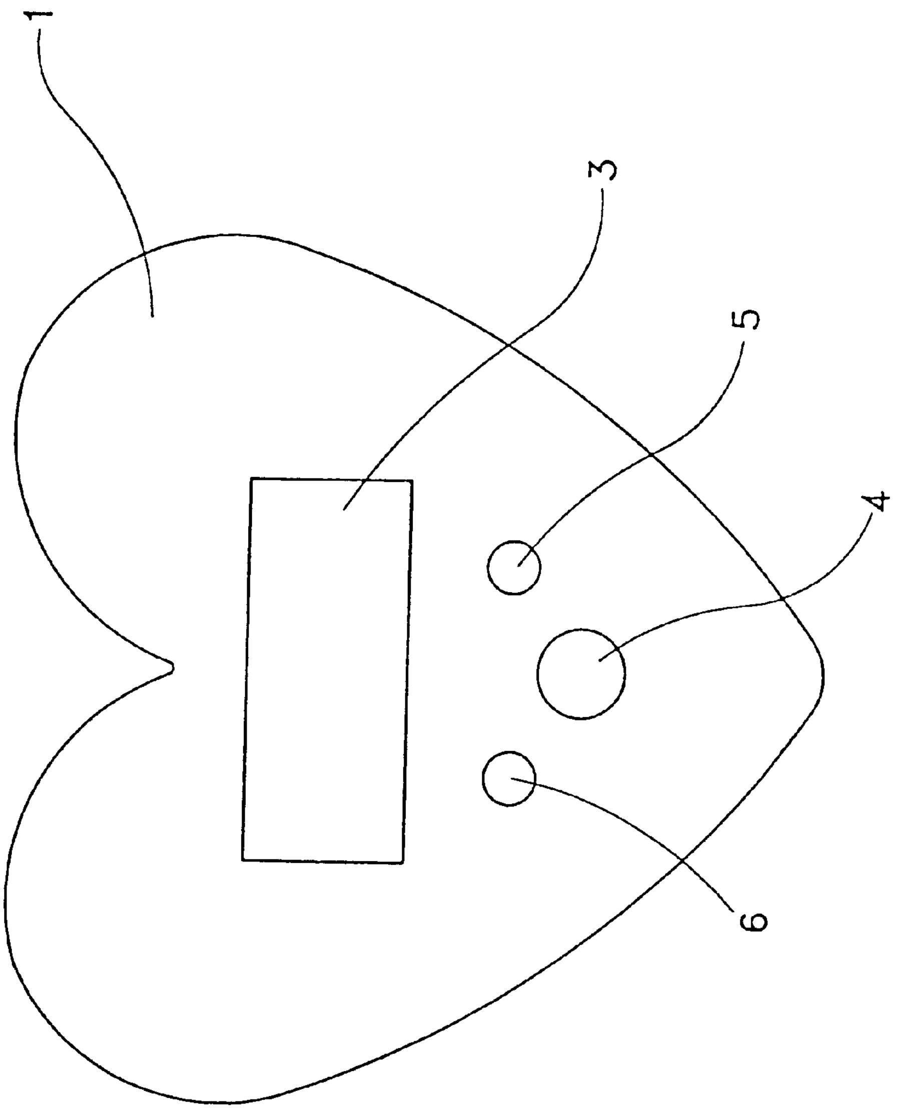
FIG. 3 is a front view of another embodiment of the present invention((—)).
Figure 4:
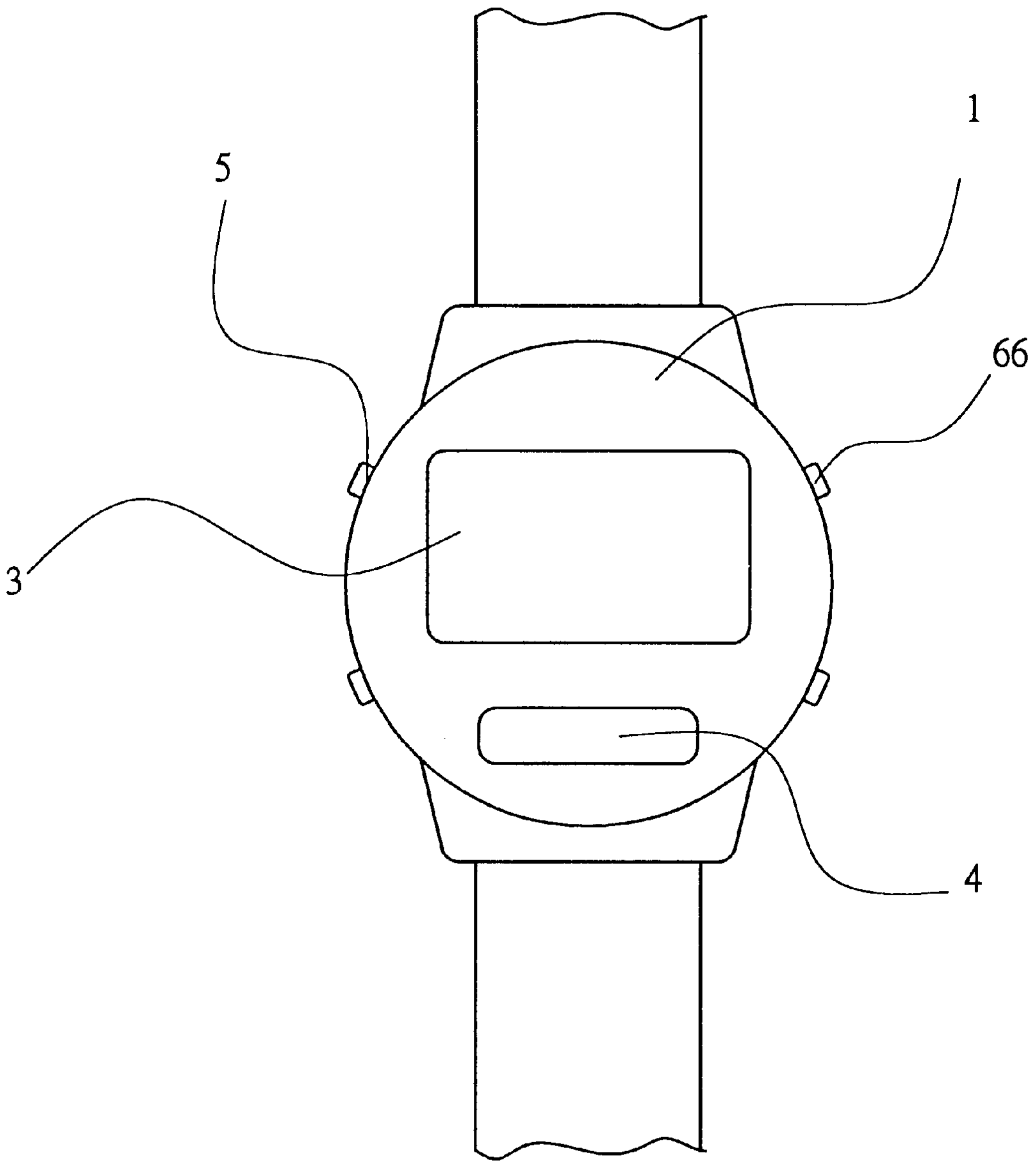
FIG. 4 is a front view of another embodiment of the present invention((—)).

Referring to FIG. 3 and FIG. 4, the pen body 1 can be designed as a housing 1' like a case, thus the shape is not confined as a pen.

Although the present invention has been described using specified embodiment, the examples are meant to be illustrative and not restrictive. It is clear that many other variations would be possible without departing from the basic approach, demonstrated in the present invention.

What is claimed is:

1. A pulse meter comprising a pen body, a counting microprocessor in said pen body, a liquid crystal display on the pen body, a manually operated counting key actuated by depression by a finger of a user to input a number of pulses felt by a different finger of the user as applied to another individual, and the counting microprocessor being connected with the LCD and the counting key;

a switching key and a time adjusting key installed on the pen body, the switching key and the time adjusting key being connected to the counting microprocessor so that the counting microprocessor can be switched to a time display mode by the switching key, wherein one hand may press a patient for sensing beats of pulses thereof, and the other hand serves to depress the counting key to count a number of the pulses, and thus a frequency of the pulses inputted to the counting microprocessor for the counting microprocessor to derive a pulse number per minute and to then display a result in the LCD.

* * * * *